United States Patent [19]

Oh

[11] Patent Number: 4,846,841
[45] Date of Patent: Jul. 11, 1989

[54] FEMORAL PROSTHESIS

[76] Inventor: Indong Oh, 851 Lyndon St., South Pasadena, Calif. 91030

[21] Appl. No.: 856,054

[22] Filed: Apr. 25, 1986

[51] Int. Cl.$^4$ ............................................. A61F 2/32
[52] U.S. Cl. ..................................................... 623/23
[58] Field of Search .................................. 623/16-23

[56] References Cited

U.S. PATENT DOCUMENTS

| | | | |
|---|---|---|---|
| 3,053,251 | 9/1962 | Black et al. | 623/22 |
| 4,005,495 | 2/1977 | Locke et al. | 623/22 |
| 4,035,848 | 7/1977 | Wagner | 623/22 |
| 4,173,797 | 11/1979 | Langlais et al. | 623/22 |
| 4,224,699 | 9/1980 | Weber | 623/22 |
| 4,274,164 | 6/1981 | Render et al. | 623/22 |
| 4,312,079 | 1/1982 | Dorre et al. | 623/22 |

FOREIGN PATENT DOCUMENTS

| | | | |
|---|---|---|---|
| 0051729 | 5/1982 | European Pat. Off. | 623/22 |
| 2297030 | 9/1976 | France | 623/22 |

OTHER PUBLICATIONS

"Total Hip Articular Replacement by Internal Eccentric Shells—The Tharies Technique for Surface Replacement", Amstutz, Harlan, M. D. Clark e, Ian PhD, Pelvifemoral Resurfacing Prosthesis, pp. 1-18.
"ICLH Cemented Double Cup Hip Replacement", Freeman M. A. R. and Brown, G. C., Archives of Orthopaedic and Traumatic Surgery, pp. 191-198.
"Double Cup Replacement of the Hip", Freeman, M. A. R., Archives of Orthopaedic and Traumatic Surgery, pp. 105-106.
"The Total Hip Arthroplasty with Bichat Cemented Matching Cups", Duparc, J., CJS, pp. 1-5.
"Tillmann Hip Re-Surfacing Prosthesis", Link America Inc., pp. 1-20.
"Total Hip Articular Replacement by Internal Eccentric Shells—The Tharies Technique for Surface Replacement"—a Second Article.
"The Aufranc Surface Replacement Hip System", Parametric Analysis of Designed Criteria for Acetabular Components of Surface Replacement Hip Devices, pp. 1-6.
"Surface Replacement Arthroplasty of the Hip of Paltrinieri-Trentani" Ranieri, L. M. D., Tretani, C. M. D., Vaccarino, F. M. D., American Academy of Orthopedic Surgeons, pp. 1-2.

Primary Examiner—Richard J. Apley
Assistant Examiner—David J. Isabella
Attorney, Agent, or Firm—Gordon L. Peterson

[57] ABSTRACT

A femoral prosthesis affixable to a remnant of a natural femoral head and cooperable with an acetabular component comprising a femoral insert having a cavity for at least partially receiving the remnant and a femoral shell having a cavity for at least partially receiving the insert. The insert is affixable to the remnant without cement, and the shell is mounted on the insert by a taper lock. The outer surface of the shell has a part-spherical region for slidably cooperating with the acetabular component to accommodate articulating motion. Selection of an appropriate combination of the insert and the shell enables hemi-surface arthroplasty or total surface arthroplasty with a minimal number of prosthetic components. Replacement of the femoral shells enables a conversion to total surface arthroplasty.

7 Claims, 2 Drawing Sheets

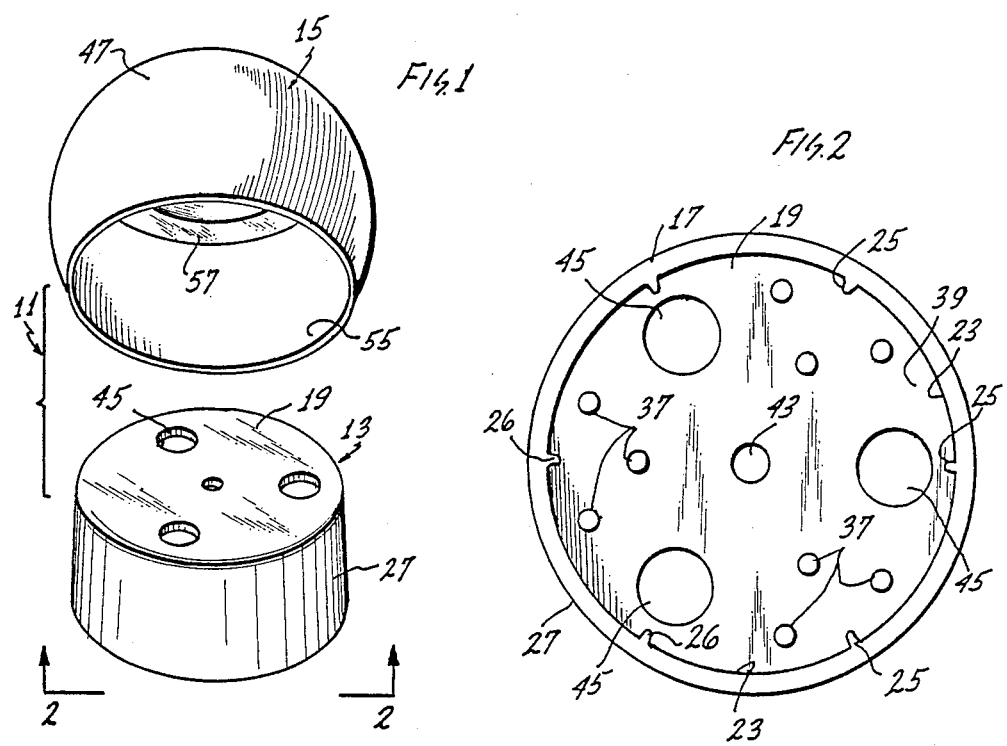
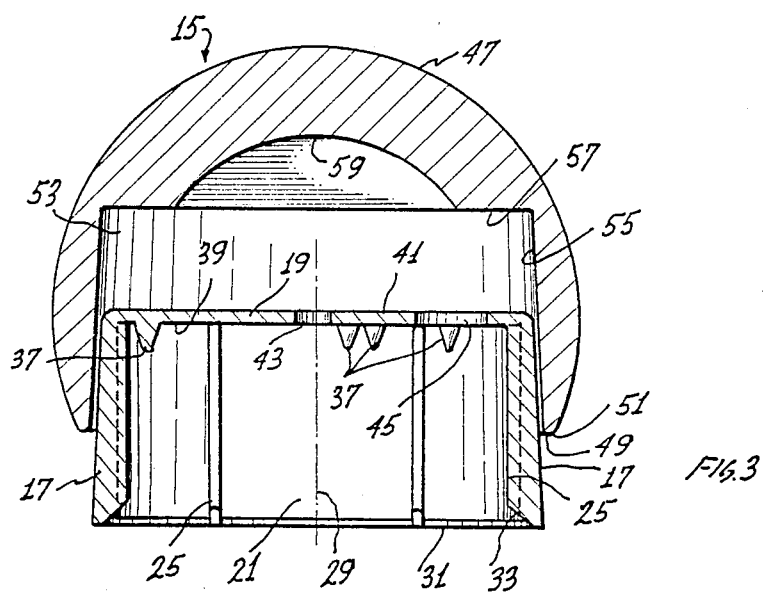

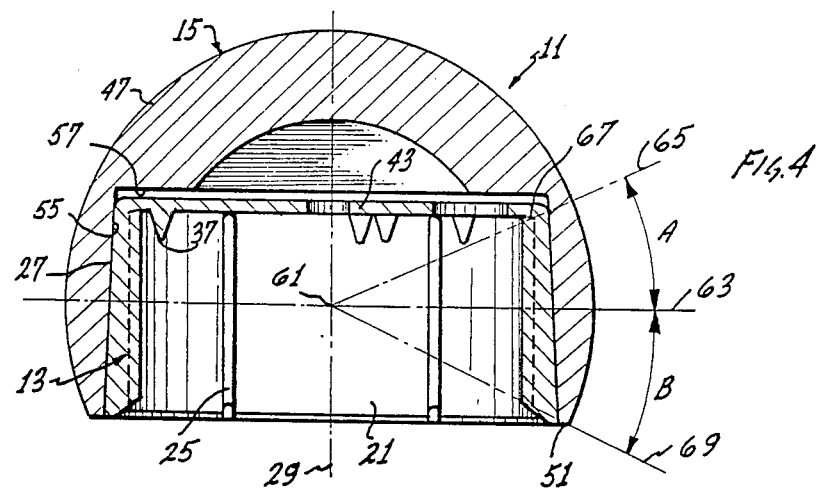
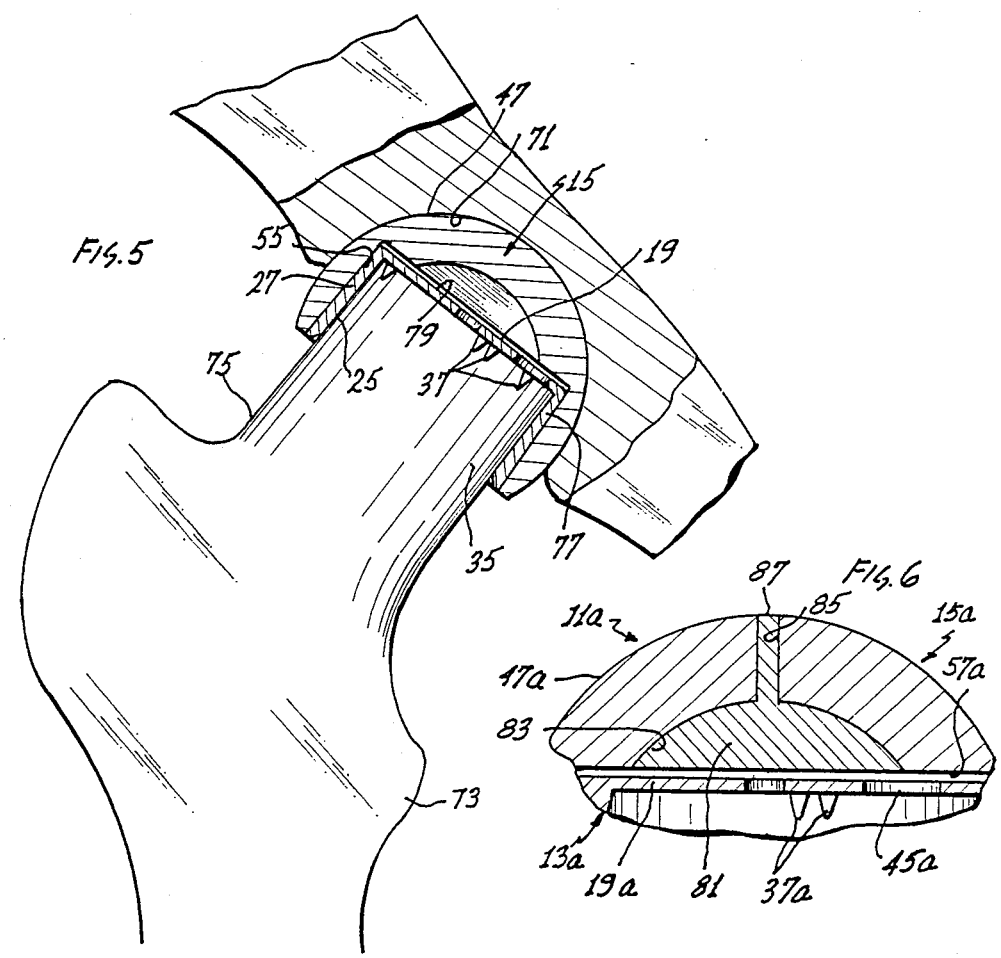
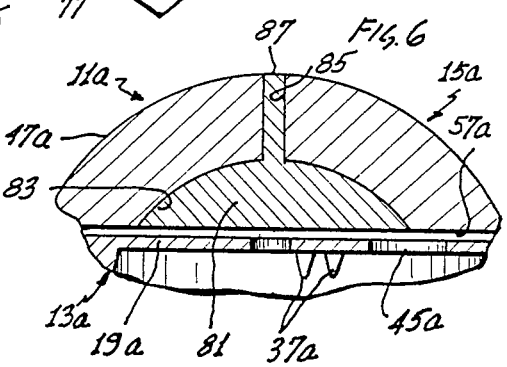

FEMORAL PROSTHESIS

BACKGROUND OF THE INVENTION

The human hip joint comprises a socket or acetabulum and a ball or femoral head. The femoral head is joined to the femur by a neck of reduced diameter and is received within the acetabulum for universal pivotal movement.

If the femoral head becomes diseased or damaged, it can be replaced with a prosthetic femoral component. The surgery includes removal of the natural femoral head and neck, and the implantation of the femoral component in the intermedullary canal of the femur. The femoral component includes a prosthetic femoral head which can cooperate with an acetabular component which may be the acetabulum, or in the case of total hip replacement, an acetabular cup.

In many cases, the diseased region of the femoral head is essentially along the surface, and the subsurface bone tissue is essentially healthy. In these situations, it is undesirable to remove the healthy portions of the femoral head and neck. Accordingly, in these cases, the diseased portion of the femoral head is removed to leave a natural femoral remnant, and a hollow femoral ball or shell is cemented onto the femoral remnant.

This construction, which is known as surface replacement, has the advantage of preserving the maximum amount of bone tissue and preserving the integrity of the intermedullary canal. In addition, it provides excellent bone stock in case of conversion surgery with a stem-type femoral prosthesis. This is a most conservative procedure which can last a long time.

Because the neck diameter varies from patient to patient, the diameter of the femoral remnant will also vary from patient to patient. Accordingly, the femoral shell must be provided with a wide range of inner diameters. The outer surface of the femoral shell must also be provided in a wide range of diameters to cover the anticipated diameters of the acetabulums and the diameters of acetabular cups that might be employed. Consequently, for each possible diameter of femoral remnant, a large number of femoral shells with different outer diameters must be provided if this procedure is going to be used by a wide range of patients. This will amount to an enormous number of prosthetic component combinations that must be held in inventory. The cost to do this is very high.

Another problem with surface replacement is that the femoral shell is cemented onto the femoral remnant. To allow a space for cement, more bone must be removed. The cement may cock the femoral shell, and it can be difficult to obtain a cement layer of even thickness.

If the acetabulum becomes diseased, it may be necessary to affix an acetabular cup within the natural acetabulum. If this should occur, it will also be necessary to replace the prosthetic femoral shell previously cemented onto the femoral remnant. When this becomes necessary, the remnant and the natural femoral neck are removed, and a stem-type prosthetic femoral component is inserted into the intermedullary canal as described above. Accordingly, if this should occur, the advantages of surface replacement are lost.

SUMMARY OF THE INVENTION

This invention retains the significant advantages of cementing the prosthetic femoral shell onto the natural femoral remnant and overcomes the disadvantages discussed above. With this invention, fewer sizes of the femoral shell need to be provided, and cementing can be eliminated. In addition, the femoral shell can be replaced in a subsequent surgery to accommodate different requirements of the acetabulum or the acetabular cup without removing the femoral remnant.

This invention provides a femoral prosthesis which comprises a femoral insert and a femoral shell. The insert has an inner surface defining a cavity open at one end for at least partially receiving the remnant of the natural femoral head, and the insert is affixable to the remnant. The femoral shell has an inner surface defining a cavity for at least partially receiving the insert and an outer surface. The shell is fixable to the insert, and at least a portion of the outer surface of the shell is part-spherical and adapted to slidably cooperate with an acetabular component to accommodate articulating motion. The acetabular component may be the natural acetabulum or any of a variety of acetabular cups.

With this invention, the femoral insert is fixed to the remnant of the natural femoral head so that a maximum amount of bone tissue is preserved and so is the integrity of the intermedullary canal. In order to fit femoral remnants of different diameters, several inserts, each having a different diameter cavity, can be provided. However, the outer surface or outer diameter of a group of the inserts can be identical so that fewer femoral shells are required. The inserts are relatively inexpensive when compared with the femoral shell because the shells must have a part-spherical, outer surface portion which is carefully and accurately constructed for cooperation with the acetabular component. The relatively inexpensive inserts adapt a femoral shell to femoral remnants of different sizes.

Although cement can be used if desired, cementless means can be used to attach the insert to the remnant and to attach the shell to the insert. Although various constructions are possible, the insert may include at least one projection on the inner surface of the insert at least partially receivable be the remnant for use in affixing the insert to the remnant of the natural femoral head. The insert preferably includes a peripheral wall and an end wall, and to best secure the insert to the remnant without the use of cement, a plurality of ribs are provided on the peripheral wall, and a plurality of pointed spikes are provided on the end wall for being driven into the remnant. The end wall of the insert preferably has at least one aperture therein so that the surgeon can observe through the aperture that the end wall and the spikes therein are substantially in contact with the remnant. The end wall can be eliminated, if desired.

Although the cementless means for affixing the shell to the insert can take different forms, preferably, it includes a taper lock on the outer surface of the insert and the inner surface of the shell. This facilitates the installation of the shell onto the insert and enables the shell to be removed from the insert in a subsequent surgery and replaced with a shell having an outer spherical portion of a different diameter thereby eliminating the need to completely remove the natural remnant and neck to change the size of the shell. By changing to a femoral shell with a smaller outside diameter, total surface arthroplasty can be achieved without removing the insert or disturbing the femoral remnant.

Although removal of the shell can be accomplished in different ways, preferably the shell has an opening in a polar region thereof, and means in the opening drivingly coupled to the insert is provided for transmitting a pushing force to the insert. Accordingly, the shell can be removed from the insert by transmitting a pushing force to the insert via such transmitting means and pulling on the shell.

It is desirable to have the greatest possible natural femoral neck diameter for a given outside diameter of the shell subject to anatomical range of motion constraints. Also, variable amounts of head resection are possible. This invention accomplishes these desirable results by establishing certain angle sizes as discussed hereinbelow.

The invention, together with additional features and advantages thereof, may best be understood by reference to the following description taken in connection with the accompanying illustrative drawing.

BRIEF DESCRIPTION OF THE DRAWING

FIG. 1 is an exploded isometric view of a femoral prosthesis constructed in accordance with the teachings of this invention.

FIG. 2 is an enlarged bottom plan view of the insert.

FIG. 3 is an axial sectional view showing the shell being slipped down over the insert.

FIG. 4 is an axial sectional view showing the shell and insert assembled, and with the femoral remnant removed to expose portions of the interior of the insert.

FIG. 5 is an elevational view partially in section showing the femoral prosthesis implanted.

FIG. 6 is a fragmentary axial sectional view similar to FIG. 4 showing a second embodiment of the invention.

DESCRIPTION OF THE PREFERRED EMBODIMENTS

FIG. 1 shows a femoral prosthesis 11 which comprises a femoral insert 13 and a femoral shell 15. The insert 13 (FIGS. 1-3), which may be constructed of a titanium alloy or stainless steel, such as chrome cobalt alloy, includes a peripheral wall 17 and an end wall 9 which cooperate to define a cavity 21 opening at an end opposite the end wall 19. The peripheral wall 17 has an inner surface 23 which, in this embodiment, is cylindrical, except for the presence of axially extending, radially inwardly extending projections in the form of ribs 25. Although various numbers of the ribs 25 may be provided, in this embodiment, six of the ribs 25 are provided, and they are equally spaced circumferentially. The ribs 25 are tapered as they extend radially inwardly so they terminate in a narrow edge 26 (FIG. 2) and may have a radial dimension of, for example, about 0.039 inch.

The peripheral wall 17 has an outer surface 27 which is configured to form a taper lock with a mating surface of the shell 15 as described below. Although various different constructions are possible, in this embodiment, the outer surface 27 is frusto-conical and decreases in diameter as it extends toward the end wall 19. By way of example and not by way of limitation, the inner surface 23 may extend axially, and the outer surface 27 may be tapered at about 5.67 degrees to a central axis 29 (FIG. 3) of the insert 13. As used herein, the taper or degree of taper, means the apex angle or cone angle of the cone formed by the frusto-conical surface.

As shown in FIG. 3, the insert 13 has an opening 31 at one end. The peripheral wall 17 has a chamfer 33 at the opening 31 to facilitate placement of the insert 13 over a femoral remnant 35 (FIG. 5) as discussed hereinbelow.

The end wall 19 is circular and has a plurality of projections in the form of spikes 37 extending generally axially inwardly from an inner surface 39 of the end wall 19 and terminating in a relatively sharp point. The spikes 37 are relatively short and may be, for example, about 0.088 inch in length. Although any desired number of the spikes 37 may be used, nine are illustrated. The end wall 19 is, except for the spikes 37, essentially a disc, and it is perpendicular to the central axis 29. The end wall 19 also has an outer surface 41, and a central aperture 43 and outer apertures 45 extend completely through the end wall 19 between the inner surface 39 and the outer surface 41. The apertures 43 and 45 can be used to visually confirm that the end wall 19 is properly seated on the remnant 35 (FIG. 5) and to provide a vent passage for air which might otherwise be trapped between the femoral remnant 35 and the insert. In addition, the aperture 43, being on the central axis 29, can be used, if desired, to position the insert on the femoral remnant 35 as described below.

The inner surfaces 23 and 39 define, or essentially define, an inner surface for the insert 13. Similarly, the outer surface 27 and the outer surface 41 cooperate to essentially define an outer surface for the insert 13.

The insert 13 can be provided in various different sizes. For example, each of the inserts 13 of one group may have different diameter inner surfaces 23, and the outer surface 27 for each insert of this group, may be of identical diameter and taper.

The shell 15 (FIGS. 1 and 3), which may be constructed of a titanium alloy or suitable stainless steel, such as chrome cobalt alloy, has a part-spherical outer surface 47 which covers the vast majority of the exterior surface of the shell. The part-spherical outer surface 47 meets an annular surface 49 (FIG. 3) along a circular termination line 51. The outer surface 47 is smooth and highly polished.

The shell 15 has an internal cavity 53 and an inner locking surface 55, which is configurated to form a taper lock with the outer surface 27 of the peripheral wall 17 of the insert 13. Although various different constructions are possible, the locking surface 55 in this embodiment is frusto-conical and decreases in diameter as it extends away from the annular surface 49. For example, the degree of taper on the locking surface 55 may be about 5.73 degrees. By employing a larger angle of taper on the locking surface 55 than on the outer surface 27, a Morse taper lock is formed so that, by pressing of the shell 15 down over the insert 13, the shell becomes locked to the insert and cannot be removed, except by the application of a substantial pulling force to the shell. Of course, other angles of taper may be employed on the surfaces 27 and 55.

The shell 15 has an annular shoulder 57 at the end of the locking surface 55, and the shoulder joins the locking surface to a central, part-spherical dome 59. The locking surface 55, the shoulder 57 and the dome 59 cooperate to define an inner surface for the shell 15, and the inner surface defines the cavity 53 within the shell.

The shells 15 can be provided in a range of diameters for the part-spherical outer surface 47 to accommodate the applicable acetabular component diameters. For example, each of the shells 15 of a group of the shells may have a different diameter for the part-spherical surface 47 and be provided with inner locking surfaces 55 of identical size and configuration so as to mate with the group of inserts 13 having a compatibly sized peripheral wall 17. This associated group of inserts serves as adapters to adapt the group of shells 15 to several different size remnants 35 so that fewer of the shells need to be provided.

FIG. 4 shows the shell 15 installed on the insert 13, with the remnant 35 not being illustrated. When so installed, the Morse taper of the surfaces 27 and 55 firmly mount the shell 15 on the insert 13. The end wall 19 is spaced from the shoulder 57 so that the shoulder does not form a hard stop for the taper lock.

When the shell 15 and insert 13 are assembled, the outer spherical surface 47 has a center 61 which lies on the central axis 29 of the insert. The prosthesis 11 has a resection angle A (FIG. 4) formed by a reference line 63 normal to the axis 29 at the center 61 and a line 65 from the center 61 through a junction 67 at the intersection of the peripheral wall 17 and the end wall 19. The prosthesis 11 also has a range of motion angle B formed by the reference line 63 and a line 69 from the center 61 to the termination line 51. The lines 63, 65 and 69 lie in the same axial plane as shown in FIG. 4.

By controlling the magnitudes of angles A and B, the amount of neck resection and range of motion are controlled. The angle A ranges from about 0 degrees to about 45 degrees, and the angle B ranges from about 20 degrees to about 40 degrees. For minimum neck resection with the greatest range of motion, the angles A and B are each about 25 degrees.

FIG. 5 shows a prosthesis 11 installed on the remnant 35 for cooperation with a femoral component which is the natural acetabulum 71. The invention is, however, equally applicable for use with acetabular components in the form of acetabular cups.

FIG. 5 shows the femur 73, the natural neck 75 and the remnant 35 of the natural femoral head. The natural femoral head has been reamed to form a generally cylindrical peripheral surface 77 and then cut as by a saw across the top to form a generally flat end surface 79 perpendicular to the axis of the cylindrical peripheral surface 77. These reaming and sawing operations remove the diseased or damaged portion of the natural head and leave an essentially healthy remnant 35.

Next, the insert 13 is installed onto the remnant 35 so as to force at least a portion of the remnant 35 into the cavity 21 of the insert 13. The inner surface 23 of the insert 13 is of a selected size such that the ribs 25 are forced to dig into the peripheral surface 77, and when the insert 13 is completely installed, the spikes 37 bite into the end surface 79 to thereby firmly mount and lock the insert onto the remnant 35. No cement is required. In the installed condition, the end wall 19 engages the end surface 79, and confirmation of this can be visually obtained during the surgery through the apertures 43 and 45. The aperture 43 may be used, if desired, with a guide pin and placement device to insure that the insert 13 does not become canted or jammed during installation. This is generally unnecessary, and therefore, the central aperture 43 can be eliminated, if desired. Although three of the apertures 45 are illustrated, this is purely illustrative and should not be taken as limiting.

Next, a shell 15 is selected from the group of shells having an interlocking surface 55 sized to form a taper lock with the locking surface 27 and also having the correct diameter on its part-spherical surface 47 to cooperate with the acetabulum 71. The shell 15 so selected is then forced over the insert 13 to place the insert in the cavity 53 and to interlock the shell and the insert to lock and fix the shell on the insert. No cement is required.

Although the taper lock is a very strong lock, it is possible to remove the shell 15 from the insert 13 in a subsequent surgery and preserve the remnant 35. This could be necessary, for example, if the acetabulum 71 became diseased and required an acetabular cup that needed a shell 15 having a part-spherical surface 47 of a different diameter.

FIG. 6 shows a prosthesis 11a which facilitates the removal of the shell 15a from the insert 13a by a pulling force on the shell. Portions of the prosthesis 11a corresponding to portions of the prosthesis 11 are designated by corresponding reference numerals followed by the letter "a." Except as shown or described herein, the prosthesis 11a is identical to the prosthesis 11.

The prosthesis 11a has a removal device 81 which fills a gap 83 between the insert 13a and the shell 15a and at least partly fills an opening 85 in a polar region of the shell 15a. More specifically, the removal device 81 has a stem 87 which is received in the opening 85 with a slight interference fit and which terminates at or slightly below the part-spherical surface 47a.

The shell 15a can be removed during a subsequent surgery by pushing against the stem 87 with a rod-like device (not shown) and applying an axial pulling force to the shell 15a. In this event, the removal device 81 provides means drivingly coupled to the insert 13a for transmitting the pushing force to the insert. If desired, the removal device 81 can be integral with the insert 13a or attached to it.

Although exemplary embodiments of the invention have been shown and described, many changes, modifications and substitutions may be made by one having ordinary skill in the art without necessarily departing from the spirit and scope of this invention.

I claim:

1. A femoral prosthesis affixable to a remnant of a natural femoral head and cooperable with an acetabular component, said prosthesis comprising:

a femoral insert having a peripheral wall and an end wall, said walls having an outer surface and an inner surface defining a cavity for at least partially receiving the remnant of the natural femoral head;

said insert having a spike on the inner surface of the end wall projecting into the cavity which can be driven into the remnant of the natural femoral head to at least assist in affixing the insert to the remnant, said cavity opening opposite said end wall;

a femoral shell having an inner surface defining a cavity for at least partially receiving the insert and an outer surface;

regions of said outer surface of the insert and inner surface of the shell being tapered radially outwardly as said regions extend away from the end wall of the insert to form a lock for locking the shell on the insert; and at least a portion of the outer surface of the shell being part-spherical and adapted to slidably cooperate with the acetabular component to accommodate articulating motion.

2. A prosthesis as defined in claim 1 wherein said end wall has at least one aperture therein.

3. A prosthesis as defined in claim 1 including a rib on the inner surface of the peripheral wall of the insert for being driven into said remnant.

4. A prosthesis as defined in claim 1 wherein a portion of said inner surface of the insert is generally cylindrical and is on the peripheral wall and a portion of the outer surface of the insert is on the peripheral wall and is frusto-conical, and said frusto-conical surface portion decreases in diameter as it extends toward the end wall.

5. A femoral prosthesis affixable to a remnant of a natural femoral head and cooperable with an acetabular component, said prosthesis comprising:
a femoral insert having a peripheral wall and an end wall, said walls having an outer surface and an inner surface defining a cavity opening at the outer surface for at least partially receiving the remnant of the natural femoral head, said insert being affixable to the remnant of the natural femoral head;
a femoral shell having an inner surface defining a cavity for at least partially receiving the insert and an outer surface, said shell being fixable to said insert, and at least a portion of the outer surface of the shell being part-spherical and adapted to slidably cooperate with the acetabular component to accommodate articulating motion; and
the part-spherical surface portion of the shell terminating along a termination line and having a center, said insert having a central axis, said center lying substantially on said axis and said peripheral wall intersecting said end wall at a juncture, said prosthesis having a resection angle formed by a first line substantially normal to said axis substantially at said center and a second line extending from said center to said juncture and a range of motion angle formed by said first line and a third line extending from said center to said termination line, said lines lying substantially in the same axial plane, each of said resection angle and said range of motion angle being about 25 degrees.

6. A femoral prosthesis affixable to a remnant of a natural femoral head and cooperable with an acetabular component, said prosthesis comprising:
a femoral insert having a peripheral wall and an end wall, said walls having an outer surface and an inner surface defining a cavity opening at the outer surface for at least partially receiving the remnant of the natural femoral head, said insert being affixable to the remnant of the natural femoral head;
a femoral shell having an inner surface defining a cavity for at least partially receiving the insert and an outer surface, said shell being fixable to said insert, and at least a portion of the outer surface of the shell being part-spherical and adapted to slidably cooperate with the acetabular component to accommodate articulating motion; and
said shell being affixed to the insert, said shell having an opening in a polar region thereof, and including transmitting means at least partially in said opening drivingly coupled to said insert for transmitting a pushing force to the insert whereby said shell can be removed from the insert by pushing on said transmitting means and pulling on the shell.

7. A prosthesis as defined in claim 6 wherein there is a gap between the outer surface of the insert and the inner surface of the shell when the shell is fixed to the insert, said gap communicates with said opening and said transmitting means includes a removal device adapted to be positioned in said gap and said opening and being engageable with said insert whereby said shell can be removed from the insert by pushing on the portion of the removal device which is in said opening of said shell and pulling on the shell.

* * * * *